United States Patent [19]

Rhodes

[11] Patent Number: 4,880,830
[45] Date of Patent: Nov. 14, 1989

[54] SLOW RELEASE FORMULATION
[75] Inventor: Alan Rhodes, Ely, United Kingdom
[73] Assignee: Ethical Pharmaceuticals Limited, United Kingdom
[21] Appl. No.: 12,026
[22] Filed: Feb. 9, 1987
[30] Foreign Application Priority Data Feb. 13, 1986 [GB] United Kingdom ............... 8603523

[51] Int. Cl.$^4$ .................. A61K 9/16; A61K 9/26
[52] U.S. Cl. .................... 424/470; 514/965; 424/468; 424/469; 424/472; 424/473
[58] Field of Search ............... 424/468, 469, 470, 472, 424/473; 514/965

[56] References Cited

U.S. PATENT DOCUMENTS

| | | | |
|---|---|---|---|
| 2,809,916 | 10/1957 | Hermelin | 424/500 |
| 2,809,917 | 10/1957 | Hermelin | 424/472 |
| 3,148,124 | 9/1964 | Gaunt | 424/468 |
| 3,279,998 | 10/1966 | Raff et al. | 424/469 |
| 3,400,197 | 9/1968 | Lippmann | 424/469 |
| 3,402,240 | 9/1968 | Cain et al. | 424/468 |
| 3,870,790 | 3/1975 | Lowey et al. | 424/469 |
| 3,946,110 | 3/1976 | Hill | 514/161 |
| 3,962,414 | 6/1976 | Michaels | 424/473 |
| 4,369,172 | 1/1983 | Schor et al. | 424/468 |
| 4,540,566 | 9/1985 | Davis et al. | 514/964 |
| 4,590,062 | 5/1986 | Jang | 424/469 |
| 4,695,467 | 9/1987 | Uemura et al. | 424/468 |
| 4,780,318 | 10/1988 | Appelgren et al. | 514/965 |

FOREIGN PATENT DOCUMENTS

| | | |
|---|---|---|
| 0013131 | 9/1980 | European Pat. Off. |
| 0094513 | 11/1983 | European Pat. Off. |
| 1021924 | 3/1966 | United Kingdom |
| 1033484 | 6/1966 | United Kingdom |
| 1137379 | 12/1968 | United Kingdom |
| 1333576 | 10/1973 | United Kingdom |
| 1405088 | 9/1975 | United Kingdom |
| 1486288 | 9/1977 | United Kingdom |

Primary Examiner—Ronald W. Griffin
Attorney, Agent, or Firm—Saidman, Sterne, Kessler & Goldstein

[57] ABSTRACT

A slow release formulation to be administered to humans or animals, comprising primary granules which contain an active ingredient and are in a secondary matrix of a water soluble/dispersible slow release material, the granules themselves comprising particles containing the active ingredients and in a primary matrix of a water soluble/dispersible slow release material.

Optionally the formulation comprises a binder phase of a water insoluble slow release material having embedded therein secondary granules comprising the secondary matrix containing the primary matrix granules.

The water soluble/dispersible material may be a polysaccharide and acacia and low viscosity methylcellulose are exemplified, as well as alginate and gelatine.

20 Claims, 4 Drawing Sheets

SLOW RELEASE FORMULATION

BACKGROUND OF THE INVENTION

1. Field of the Invention

The present invention relates to a slow release formulation for pharmaceutical or veterinary use.

2. Description of the prior art.

The use of slow release formulations (also known as controlled release or sustained release formulatitons) is well established in medicine and the value of slow release formulations is widely appreciated. Slow release formulations have the advantage that the active compound is released over a relatively long period so that the active compound is maintained in the blood stream for a longer time and at a more uniform concentration than would otherwise be the case. It is also known to formulate slow release preparations to release the active compound only when the preparation has reached a certain part of the digestive system.

Many different proposals have been put forward for slow release formulations. One proposal for a slow release formulation is put forward in British Pat. No. 1021924: in the process of this patent the medicament is admixed with a comminuted sustained release material to obtain a dry mixture which is subsequently pressed into tablets. The sustained release material is said to be advantageously used in amounts of as much as 95%, a very high proportion indeed.

It is also known to prepare slow release formulations by incorporating active ingredient in a water insoluble binder which will disperse only very slowly in the alimentary system. For example, British Pat. No. 1137379 discloses a multi-stage formulation process in which ethylcellulose (which is water insoluble) is used as binder in the initial step. It would appear that in GB 1137379 insufficient alcohol is used in the initial processing to dissolve the ethylcellulose and thus a matrix (i.e. a uniform, continuous phase) is not formed. The process disclosed is very complex and would not be economical.

Another controlled release formulation which utilizes a water insoluble polymer is U.S. Pat. No 3,962,414. The polymer of U.S. Pat. No. 3,962,414 is initially water soluble but is cross-linked with polyvalent metal cations in the final formulations, and the patent discloses three different structures which use the cross-linked polymer to release drugs to the eye.

British Pat. No. 1486288 describes a water insoluble matrix which holds an active substance (e.g. a drug). EP 0094513 covers a device having not a water soluble matrix but a biodegradable one. The device is suitable for use as an implant, because the release of active material has a duration of several months or more and is achieved by biodegradation of the polymers comprising the system.

U.S. Pat. No. 2,809,916 discloses a formulation process using repeated steps (processes using 9 to 15 steps are exemplified) of mixing a drug with water insoluble excipient, drying and granulating. At each granulation step the mix is granulated to the same size and the result of such a process is a uniform and intimate mixture of excipient and active ingredient. The reason for carrying out the multistage process is apparently that sufficient excipient could not be combined with the active ingredient in one step - if all the excipient were added in one step the result would be an unworkable slurry. The US patent states that by increasing the number of mixing-drying steps the rate of release of the drug is slowed but it is to be expected that when the amount of insoluble binder is increased in this way the rate of release will be slowed.

A two stage formulation process is also disclosed in Example 8 of U.S. Pat. No. 3,946,110, in which aspirin powder is first mixed with pectin, then granulated and mixed with potato starch and silica. The potato starch, however, acts not as a slow release binder but as a disintegrator to accelerate release of aspirin. The inclusion of silica is for absorption of atmospheric moisture before this has a chance to react with the aspirin to form acetic and salicylic acids.

I have now appreciated that there remains a need for an economical slow release formulation. In particular, it would be desirable to provide slow release formulations which need only include cheap and readily available excipients and which can be made using existing machinery.

SUMMARY OF THE INVENTION

I have now discovered that the rate of release of active ingredient in water soluble/dispersible matrix material may be slowed by arranging the active ingredient in a novel physical arrangement in the matrix material.

Accordingly, the present invention provides a slow release formulation to be administered to humans or animals which uses water soluble/dispersible binder or binders (which must inherently take time to dissolve or disperse) to control the release of the active ingredient. The formulation comprises secondary granules which comprise primary granules within a secondary matrix of a water soluble/dispersible slow release material, the primary granules themselves comprising particles comprising an active ingredient within a primary matrix of a water soluble/dispersible slow release material.

Also included in the invention is a method of making slow release formulations. In the method, particles comprising an active ingredient are mixed together with a solution or dispersion of a water soluble/dispersible slow release material, to form an agglomerate and is granulated. The resultant primary granules, after drying, are mixed together with a solution or dispersion of a water soluble/dispersible slow release material to form an agglomerate. The agglomerate is then granulated to form secondary granules of a larger size than the primary granules and dried. The second granulation step is necessary to obtain a suitable dosage form for administration. The secondary granules as such could be used as the dosage form and could be administered by, for example sprinkling on food. More usually, however the second granulation step is necessary for further processing to form tablets or capsules for oral administration. Although oral dosage forms are preferred, it is envisaged that the secondary granules could be incorporated in suppositories or implants.

The slow release formulations of the invention may be called "multi-matrix formulations", since they comprise at least a primary matrix of slow release material binding the particles containing the active ingredient to form primary granules and a secondary matrix of slow release material which binds the primary granules together. Surprisingly, we have found that a multi-matrix formulation releases the active ingredient over a substantially longer period than a single matrix formulation containing the same proportions of active ingredient and slow release material.

The slow release formulations of the invention may alternatively be defined as comprising particles which comprise an active ingredient and are arranged as clusters of relatively densely packed particles dispersed in water soluble/dispersible matrix material. The matrix material at the clusters (i.e. the primary matrix) may be the same as or different to the matrix material between the clusters (i.e. the secondary matrix).

The method of the invention is a "building up" process in which, because the second granulating step produces larger granules than the first step, there is built up the non-uniform or discontinuous multi-matrix structure. This method should be distinguished from the homogenising multi-stage granulation process of U.S. Pat. No. 2,809,916 in which each granulation is to the same size and there is no building up and a uniform structure is achieved which is continuous in the sense that there are no sharp changes in the pattern of medicament dispersion.

The invention is not restricted as to the active ingredient and any one or more active ingredients may in principle be used. For example, the formulations may contain aminophylline, theophylline or another bronchodilator, for the treatment of asthma or bronchitis. Alternatively, the active ingredient may, for example, be a tranquiliser, e.g. hydroxyzine, chlordiazepoxide or chlorpromazine hydrochloride. Other possible active ingredients are analgesics (e.g. morphine), antibiotics or antihypertensives (e.g. propranalol).

The same or different slow release materials may be used in the different matrixes. The water soluble or water dispersible material of the matrixes may be any such material which can be used as a pharmaceutical or, appropriately, veterinary binder and which is slowly soluble in water and/or poorly wetted by water, e.g. a cellulose derivative, especially methylcellulose, or other polysaccharide. Another preferred water soluble/dispersible binder is acacia (gum arabic), optionally in admixture with another binder, such as tragacanth, agar, sterculia or starch, for example. When in admixture, the acacia generally forms substantially 50 wt % or more of the mixture. Some or all of the acacia may be replaced with apricot gum.

Other preferred water soluble/dispersible binders are gelatine and alginates.

The matrixes consist of water soluble and/or dispersible materials which can thus be applied in an aqueous medium. In the case of active ingredients which might be adversely affected by water (e.g. would be susceptible to hydrolysis) it may be preferable to use a pharmaceutically acceptable organic solvent or dispersant, for example a lower alkanol, especially methanol, ethanol or isopropanol, or a haloalkane, especially chloroform or methylene chloride. Suitable mixtures may also be used, e.g. aqueous ethanol or methanol.

Matrix material is used in the process in solution or dispersion to ensure thorough mixing with the admixed material and the formation of a homogeneous matrix structure.

The secondary granules may be bound in a binder phase of a water insoluble slow release material. If a water insoluble slow release material is used to bind granulated double matrix composition, a lipid material as described in British Pat. No. 1021924 may be chosen to form the binder phase. We have found hydrogenated castor oil to be satisfactory but any other lipid material referred to in GB 1021924 may be used, for example. As examples there may be mentioned mineral, vegetable or animal waxes, a $C_{24}$–$C_{62}$ ester of a $C_{12}$–$C_{31}$ fatty acid and $C_{12}$–$C_{31}$ fatty alcohol, a $C_{10}$–$C_{22}$ fatty acid, a $C_{10}$–$C_{22}$ fatty alcohol or a mono-, di- or triglycerol ester of a $C_{10}$–$C_{22}$ fatty acid. Especially preferred are hydrogenated castor oil, glyceryl mono- or disterate, 12-hydroxystearyl alcohol and micro-crystalline wax. The reader is referred to GB 1021924 or its equivalent U.S. Pat. No. 3,279,998 for further information. U.S. Pat. No. 3,279,998 is included herein by reference.

In addition to the active ingredient and the slow release materials, the formulations of the invention may include other components in any portion of the formulation, for example fillers (e.g. lactose, bentonite, calcium phosphate, glycine, calcium carbonate, kaolin, sucrose), lubricants (e.g. boric acid, cacao oil, paraffin, polyethylene glycol, talc, stearates, stearic acid), preservatives (e.g. methyl or ethyl p-hydroxybenzoate), absorption promoters (e.g. glycerin mono-or di-medium sized alkanoates), antioxidants, flavourings, edible colouring agents and stabilizing agents.

The formulations of the invention may be formulated into forms for oral administration (e.g. tablets or capsules) and may be for either medical or veterinary use. In the preparation of tablets or capsules, the secondary granules may be dispersed in a water insoluble binder phase as described above prior to being formed into tablets or capsules. If desired, the tablets or capsules may be enteric, film or sugar coated. Instead of being formulated into oral dosage form, it would be feasible to process the formulations of the invention into suppositories or implants, in which case the secondary granules would generally be embedded in a water insoluble binder phase.

The proportions of the different ingredients are not critical but the sustained release material of the matrixes generally amounts to about 1 to about 50% by weight of the total solids of the matrix material and the particles containing the active ingredient. Preferably, the amount of the sustained release material of the matrixes is of from about 1.5 to about 15% by weight of the total solids of the matrix material and the particles containing the active ingredient. The particular amount of sustained release material chosen will vary from application to application and can be determined by the skilled person for each case.

The active ingredient or ingredients plus any diluents generally form from about 50 to about 99%, more usually from about 85 to about 98.5% by weight of the total solids of the matrixes and the particles containing the active ingredients.

If the formulations include a water insoluble binder phase, this may constitute from about 1 to about 50% by weight of the total solids of the formulation, for example, although in some instances higher quantities might be desirable. Preferably, the binder phase amounts to about 5 to about 25% by weight of the total solids.

Other minor ingredients generally amount to a few percent of the total solids of the formulations, e.g. from about 0.5 to about 5% by weight.

DETAILED DESCRIPTION OF THE INVENTION.

Figure 1:
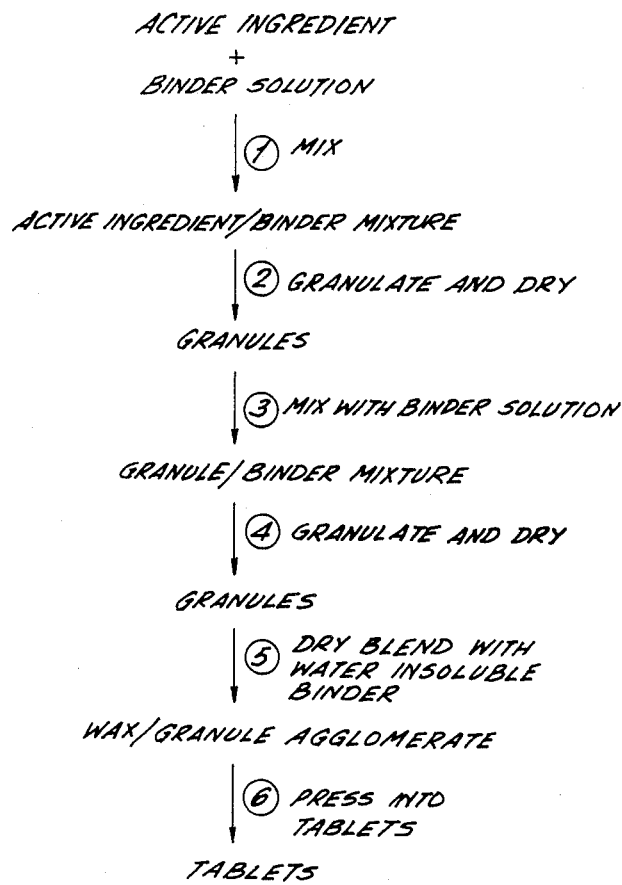
FIG. 1 is a flow chart illustrating a method of preparation of the formulations of the invention.

Turning to FIG. 1, in a preferred method of the invention, a powder of the active ingredient is blended, for example in a conventional mixer, with an aqueous solution or dispersion of a water soluble or dispersible sustained release binder to form an agglomerate. The solution or dispersion is desirably relatively concentrated, for example a solution of 1 part by weight of acacia in 1 to 2 parts, preferably 1.25 to 1.8 parts, by weight of purified water. The use of a concentrated solution makes handling and drying of the resultant mixture relatively easy.

The wet agglomerate is then dried, for example on a fluid bed drier. A temperature of 35° C. to 60° C. is suitable for the drying. After being dried, the mixture is passed through a dry granulator of rlatively fine mesh aperture (e.g. 600 um to 250 um mesh aperture, preferably 500 to 355 um) and, if necessary, may be further dried.

The single matrix granules now obtained are then subjected to the same procedure again. They are mixed with binder solution (often but not necessarily the same solution as used in the first stage), dried and granulated (generally to 2 mm to 1 mm mesh aperture) to obtain secondary granules.

Step 5 of FIG. 1 is optional and thus the secondary granules may now be directly compressed into tablets or encapsulated or they may be dry blended with a water insoluble binder (e.g. hydrogenated castor oil) and compressed in a tablet press. The tablets may subsequentlty be coated, e.g. with an enteric coating. It will be seen that the whole process may be carried out using conventional apparatus. Of course, the secondary granules may be processed into a dosage form other than tablets or capsules.

Figure 2:
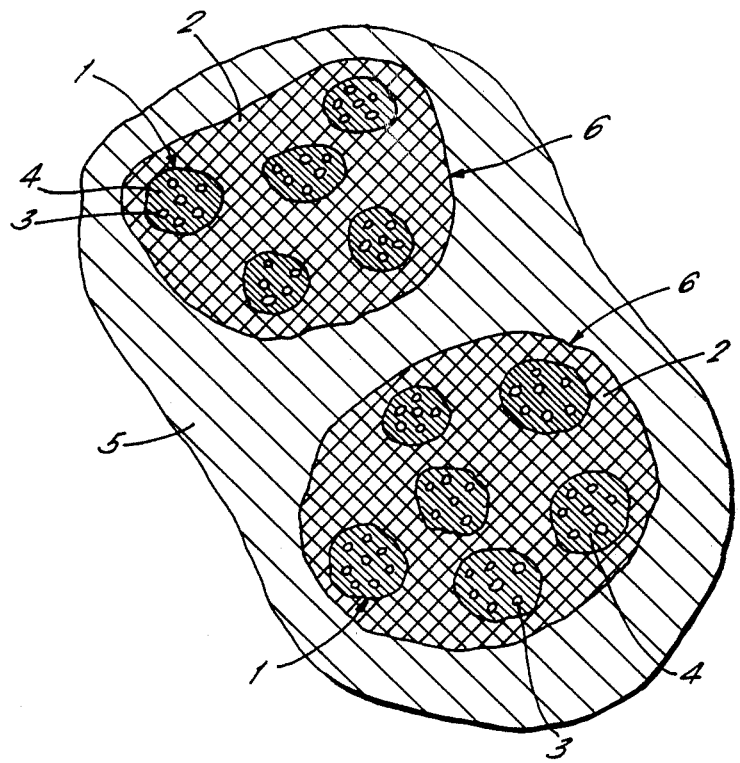
FIG. 2 is a schematic illustration of a formulation prepared by the method illustrated in FIG. 1.

FIG. 2 is a schematic cross-section through a portion of a tablet obtained after step 6 of the process of FIG. 1. The tablet comprises a binder phase 5 of a water insoluble binder in which there are embedded double matrix or secondary granules 6 containing the active ingredient. The secondary granules 6 themselves comprise single matrix or primary granules 1 in a secondary matrix 2 of sustained release binder. In turn, the primary granules 1 comprise particles 3 containing the active ingredient in a primary matrix 4 of sustained release binder.

If desired, the above described process may be modified by adding to the formulation at an appropriate stage a filler or other additional component.

The above described process may be modified in a number of ways, as will be apparent to the skilled person. For example, when using methylcellulose as one or both matrixes it might be advantageous in steps 1 and/or 3 of FIG. 1 to, firstly, dry blend high viscosity methylcellulose and, respectively, the particles containing the active ingredient or the single matrix granules and subsequently to mix the dry blend with a solution of low viscosity cellulose. Alternatively, the slow release material of one or both matrixes could initially be dry blended with the particles containing the active ingredients or the single matrix granules and subsequently water or another liquid (e.g. ethanol) would then be added to the dry blend and mixed therewith.

The water insoluble binder, instead of being dry blended with the double matrix granules could be added as a melt or in an organic solvent, for example ethanol.

It is further contemplated that the process could be modified to obtain triple matrix granules by repeating steps 3 and 4 of FIG. 1 after step 4. However, in this case in stage 2 the mixture would generally be granulated more finely then would otherwise be the case, and the third granulation step would be to a larger granule size than the second granulation step.

The following Examples illustrate the invention:

EXAMPLE 1

| FORMULA | |
|---|---|
| First Mix | |
| Aminophylline | 1000 g |
| Acacia | 50 g |
| Purified water | 75 ml |
| Second Mix | |
| Acacia | 50 g |
| Purified water | 75 ml |
| Binder Phase | |
| Cutina HR (Hydrogenated castor oil) | 200 g |

Method (1) Add the 50 g acacia dissolved in 75 ml water to the aminophylline in a mixer (Baker Perkins) under conditions of 100 rpm main impeller. Increase the speed to 500 rpm main/1000 rpm side and mix for 5 minutes. Scrape down and mix for 5 minutes and scrape down again and mix for a further 5 minutes.

(2) Discharge the formed granules, fluid bed dry at 40° C. for 5 minutes and granulate to 500 um mesh aperture size.

(3) Granulate to 355 um mesh aperture size and fluid bed dry for 5 minutes at 40° C.

(4) Place the dried granules back into the mixer and mix in the second portion of acacia dissolved in water.

(5) Granulate to 1.4 mm mesh aperture size, fluid bed dry at 40° C. for 5 minutes, and repeat this procedure twice.

(6) Blend in the Cutina and compress under power in a Manesty F3 tablet press.

There were obtained 20 smooth white to light grey tablets free from pits or blemishes with a slightly discernable matrix structure.

| Dissolution in water | |
|---|---|
| Mean Amount dissolved in 1 hr = | 48% |
| Mean Amount dissolved in 2 hr = | 69% |
| Mean Amount dissolved in 3 hr = | 85% |
| Mean Amount dissolved in 4 hr = | 94% |

| -continued |  |
|---|---|
| Dissolution in water | |
| Mean Amount dissolved in 5 hr = | 98% |

The dissolution rate obtained with tablets of the invention was compared with conventional single matrix tablets prepared by the procedure given in the following Comparative Example.

Comparative Example

FORMULA

| Aminophylline | 100 g |
|---|---|
| Acacia | 10 g |
| Purified water | 15 ml |
| Cutina HR | 20 g |

Method

The acacia in water was mixed with the aminophylline using a mortar and pestle before drying and granulating to form a 1.4 mm mesh aperture size granule. The Cutina was then dry blended and the product compressed under power on a Manesty F3 tablet press.

Dissolution

| Mean Amount dissolved in 1 hr = | 70% |
|---|---|
| Mean Amount dissolved in 2 hr = | 97% |

Figure 3:
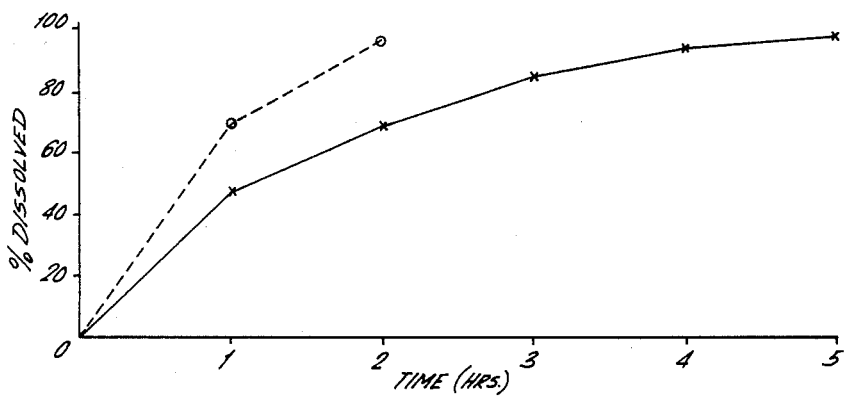
FIG. 3 is a graph comparing the dissolution of a formulation of the invention with a single matrix formulation prepared with the same ingredients in the same proportions.

The use of a single as opposed to double matrix of acacia for the aminophylline granules has resulted in an unexpectedly drastic increase in the rate of tablet dissolution as best demonstrated by FIG. 3, which is a graph of the dissolution rates of the tablets obtained in Example 1 and those obtained in the Comparative Example.

In vivo study of the tablets obtained in accordance with the general method of Example 1

Figure 4:
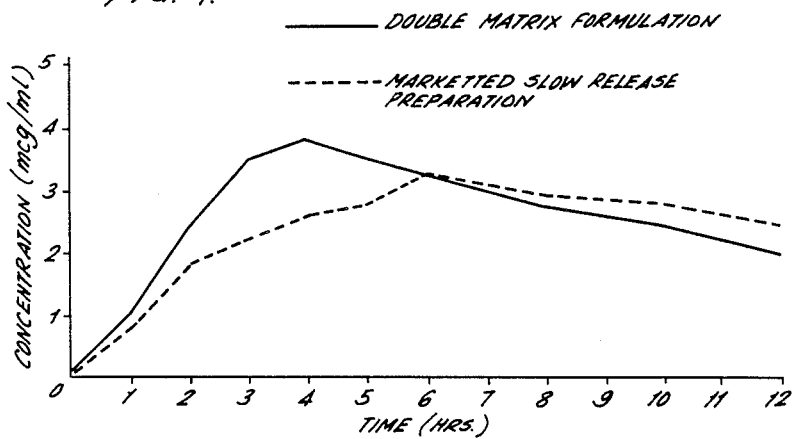
FIG. 4 is a graph of mean plasma theophylline concentration following administration to volunteers of an aminophylline formulation of the invention and a comparative single matrix formulation.

A study was undertaken in 4 healthy young volunteers wherein on each of 2 separate occasions, separated by at least a seven day washout period to permit "washing out" of aminophylline from the volunteers, each subject was administered either a 225 mg aminophylline tablet prepared using a method like that of Example 1, or a commercially available 225 mg slow release aminophylline tablet formulated in accordance with British Pat. No. 1405088. Blood samples were obtained on administration of each test preparation and at suitable time intervals thereafter and subsequently analysed for plasma theophylline concentration (the active moiety of aminophylline). FIG. 4 shows the mean plasma theophylline concentration versus time profiles obtained. As can be seen the tablets produced according to the present invention result in plasma theophylline concentrations similar to those obtained by the marketted slow release aminophylline preparation.

Example 2

| Formula | Amount |
|---|---|
| Theophylline Monohydrate | 1100 g |
| Methyl Cellulose (low viscosity) | 20 g |
| Purified Water | 450 ml |
| Talc | 11 g |
| Mg. stearate | 11 g |

Utilising the above formula batch 1 was processed according to the double matrix procedure and batch 2 was processed by a single matrix procedure. Both batches utilised a solution of the methyl cellulose in water and both were processed to a final granule size of 1.4 mm prior to dry blending with the lubricants (talc and magnesium stearate) and compression to 400 mg anhydrous theophylline tablets.

On testing for dissolution in degassed, distilled water at 37° C. using the USP 'Paddle' procedure, at 100 rpm mixing speed, the two batches gave the following results.

| | % in solution | |
|---|---|---|
| Time (hrs.) | Batch 1 (Double Matrix) | Batch 2 (Single Matrix) |
| 1 | 17 | 20 |
| 2 | 24 | 32 |
| 3 | 31 | 44 |
| 4 | 37 | 54 |
| 5 | 41 | 64 |
| 6 | 47 | 72 |
| 7 | 51 | 80 |
| 8 | 55 | 89 |

Figure 5:
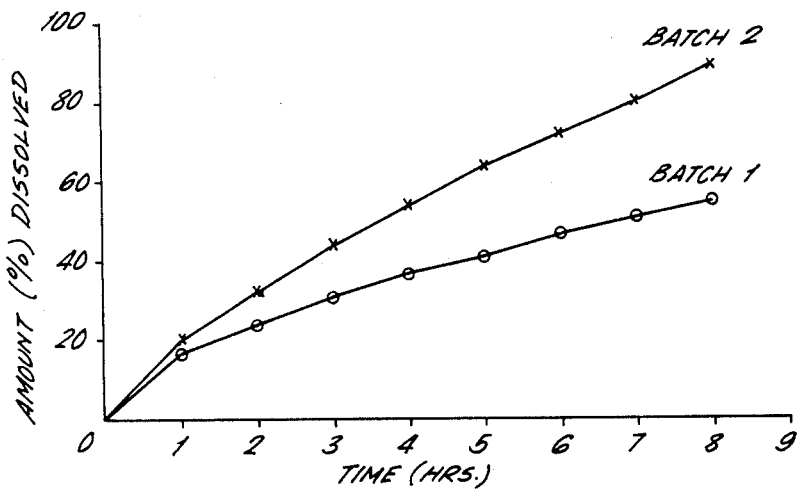
FIG. 5 is a graph illustrating the influence of double matrix processing of a theophylline/methyl cellulose formulation.

These results are further presented graphically in FIG. 5 where the difference in rates of dissolution of the two preparations becomes very apparent.

Figure 6:
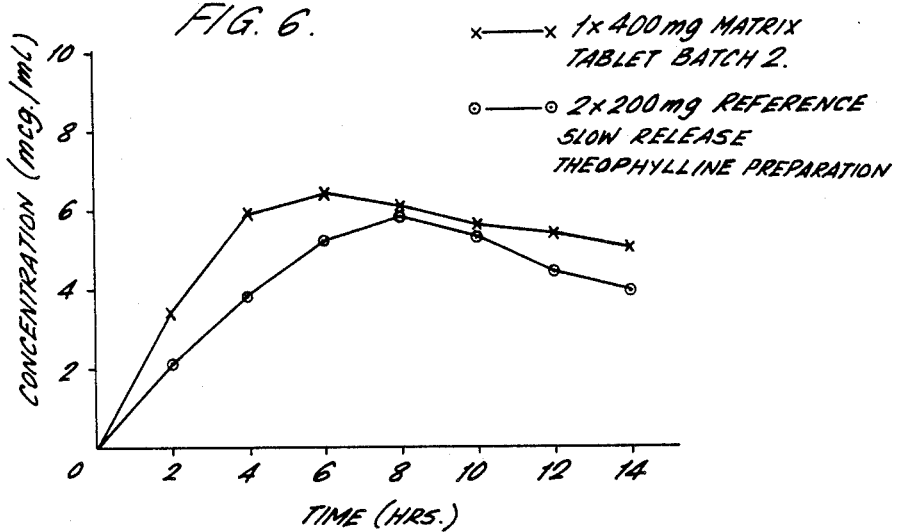
FIG. 6 is a graph of mean plasma theophylline concentration following administration to volunteers of a double matrix theophylline formulation of the invention and a comparative marketed slow release formulation manufactured in accordance with British Pat. No. 1405088, which is included herein by reference.

Again the double matrix formulation (Batch 1) was used in a bioavailability study (4 subjects), the results of which are shown in FIG. 6 in comparison to a single dose of 2×200 mg tablets of the reference slow release theophylline preparation. As before tablets prepared according to the present invention produced very similar results to those obtained with the reference marketed slow release theophylline tablets.

EXAMPLE 3

The use of sodium alginate as the matrix material is shown in this Example.

| Formula | Amount |
|---|---|
| Theophylline Monohydrate | 550 g |
| Sodium Alginate | 10 g |
| 95% Ethanol | 20 ml |
| Purified Water | 250 ml |
| Magnesium Stearate | 5.6 g |

In the above formula the ethanol is present as a dispersant for the sodium alginate to enable thorough dissolution in the aqueous granulating medium. Batches 3 and 4 were respectively processed by the single and double matrix procedures using the above formula. Finished tablets from the 2 batches were assessed for dissolution rate by the USP 'Paddle' procedure; degassed distilled water @ 37° C.; 100 rpm paddle speed to yield the following data:

| | % in solution | |
|---|---|---|
| Time (hrs) | Batch 3 (Single Matrix) | Batch 4 (Double Matrix) |
| 1 | 44 | 34 |
| 2 | 76 | 61 |
| 3 | 94 | 87 |

Again the slowing of dissolution when tablets are processed by the double as opposed to single matrix method is readily apparent.

EXAMPLE 4

Gelatine may also be used as the matrix former as shown by this Example:

| Formula | Amount |
|---|---|
| Theophylline Monohydrate | 550 g |
| Gelatine | 25 g |
| Purified Water | 125 ml |
| Magnesium Stearate | 5.75 g |

This particular formulation is processed by initially dissolving the gelatine in hot water. Processing may then be continued as previously described. In this Example the batches produced were 5 (single matrix) and 6 (double matrix) which on dissolution testing (conditions as in Example 3) produced the following results:

| | % in solution | |
|---|---|---|
| Time (hrs) | Batch 5 (Single Matrix) | Batch 6 (Double Matrix) |
| 1 | 58 | 51 |
| 2 | 91 | 83 |

Again the double matrix formulation is seen to exhibit a more prolonged dissolution profile than the single matrix preparation. However, it is also apparent from all the examples that dissolution rate is also dependant on the type as well as amount of the matrix materials used. It is therefore apparent that the invention provides scope for the production of slow release preparations of widely differing specifications so that the exact profile required may be obtained by successive experimentation.

It will be seen from the foregoing that we have provided controlled release formulations which need use only cheap and readily available slow release materials (e.g. water soluble or dispersible polysaccharides) which can be readily and easily formulated with active compound by mixing the active compound with the slow release material in a liquid dispersion or solution. No. special materials or machinery is required.

Optionally, the granulated double matrix composition may be dispersed in a binder phase of a water insoluble slow release material, if needed to achieve the desired controlled release characteristics. This option enhances the flexibility of the invention. It is also envisaged that the invention could be modified by carrying out at least a third granulation step to obtain tertiary granules which could subsequently be processed in the same manner as the secondary granules.

From the foregoing, one skilled in the art can ascertain the essential characteristics of the invention and, without departing from the spirit and scope thereof, can make various changes and modifications of the invention to adapt it to various applications and conditions.

What is claimed is:

1. A slow release formulation to be administered to humans or animals, comprising (1) granules which comprise particles comprising an active ingredient and a primary matrix of water soluble/dispersible slow release material in which are dispersed said particles comprising the active ingredient, and (2) a secondary matrix of a water soluble/dispersible slow release material in which said granules are dispersed.

2. A slow release formulation as claimed in claim 1 wherein both matrixes are formed of the same slow release material.

3. A slow release formulation as claimed in claim 1 wherein said slow release material of at least one of said matrixes is selected from the group consisting of polysaccharide material, alginate and gelatine.

4. A slow release formulation as claimed in claim 3 wherein said polysaccharide material is selected from the group consisting of acacia, a mixture comprising at least 50 wt % acacia and another binder, and low viscosity methylcellulose.

5. A slow release formulation as claimed in claim 1 wherein said secondary matrix/granule composition is itself in the form of granules and is in a binder phase of a water insoluble slow release material.

6. A slow release formulation as claimed in claim 3 wherein said secondary matrix/granule composition is itself in the form of granules and is in a binder phase of a water insoluble slow release material.

7. A slow release formulation as claimed in claim 6 wherein said water insoluble slow release material is selected from the group consisting of mineral, vegetable or animal wax, $C_{24}$–$C_{62}$ esters of a $C_{12}$–$C_{31}$ fatty acid and $C_{12}$–$C_{31}$ fatty alcohol, $C_{10}$–$C_{22}$ fatty acids, $C_{10}$–$C_{22}$ fatty alcohols, mono-, di- and triglyceryl esters formed from a $C_{10}$–$C_{22}$ fatty acid, and mixtures thereof.

8. A slow release formulation as claimed in claim 7 wherein said water insoluble slow release material is selected from the group consisting of hydrogenated castor oil, glyceryl mono- and distearate, 12-hydroxystearyl alcohol, micro-crystalline wax and mixtures thereof.

9. A slow release formulation as claimed in claim 3 and formulated for oral administration.

10. A method of making a slow release formulation to be administered to humans or animals, comprising mixing particles comprising an active ingredient and a solution or dispersion in a liquid vehicle of a water soluble/dispersible slow release material to form an agglomerate and granulating said agglomerate to form primary granules, drying said primary granules and then mixing them with a solution or dispersion in a liquid vehicle of a water soluble/dispersible slow release material to form an agglomerate and granulating said agglomerate to form secondary granules of a larger size than said primary granules, and drying said secondary granules.

11. A method as claimed in claim 10 wherein each said liquid vehicle is independently selected from the group consisting of water, ethanol, methanol, aqueous ethanol, aqueous methanol, chloroform, isopropanol and methylene chloride.

12. A method as claimed in claim 10 in which the or each water soluble/dispersible material is selected from the group consisting of polysaccharide material, alginate and gelatine.

13. A method as claimed in claim 10 wherein there are two granulating steps and in the first granulating step said agglomerate is granulated to a size of 600 um to 250 um mesh aperture and in the second granulating step said agglomerate is granulated to a size of 2 mm to 1 mm mesh aperture.

14. A method as claimed in claim 10 wherein said particles containing active ingredient or said primary granules or both are dry blended with high viscosity methylcellulose and subsequently admixed with a solution/dispersion of low viscosity methylcellulose.

15. A method as claimed in claim 10 which further comprises blending said secondary granules with a water insoluble slow release material.

16. A slow release formulation to be administered to humans or animals, comprising particles comprising an active ingredient and water soluble/dispersible matrix material, said particles being arranged as clusters or relatively densely packed particles dispersed in said water soluble/dispersible matrix material, said matrix material at said clusters optionally being different to said matrix material between said clusters.

17. A slow release formulation as claimed in claim 16 wherein said matrix material at said clusters is the same as said matrix material between said clusters and said matrix material is selected from the group consisting of polysaccharide material, gelatine and alginate.

18. A slow release formulation as claimed in claim 16 wherein said matrix material with said particles dispersed therein is in the form of granules and said granules are in a binder phase of a water insoluble slow release material.

19. A slow release formulation as claimed in claim 16 and formulated for oral administration.

20. A method of treating a human or animal for a disease, comprising orally administering to said human or animal an oral dosage form comprising an active ingrdient for treating said disease, said active ingredient being arranged in particles dispersed in a primary matrix of water soluble/dispersible slow release material, said primary matrix with said particles dispersed therein being formed as granules and said granules being dispersed in a secondary matrix of water soluble/dispersible material, said secondary matrix and said primary matrix being formed of the same or different slow release material.

* * * * *